US008915956B2

(12) United States Patent
Schaeffer et al.

(10) Patent No.: US 8,915,956 B2
(45) Date of Patent: Dec. 23, 2014

(54) PROSTHESIS WITH MOVEABLE FENESTRATION

(75) Inventors: Darin G. Schaeffer, Bloomington, IN (US); Shyam Kuppurathanam, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 641 days.

(21) Appl. No.: 12/548,120

(22) Filed: Aug. 26, 2009

(65) Prior Publication Data

US 2010/0063576 A1   Mar. 11, 2010

Related U.S. Application Data

(60) Provisional application No. 61/093,202, filed on Aug. 29, 2008.

(51) Int. Cl.
 A61F 2/06   (2013.01)
 D03D 3/02  (2006.01)
 A61F 2/07   (2013.01)
 A61F 2/89   (2013.01)

(52) U.S. Cl.
 CPC ............ *D03D 3/02* (2013.01); *A61F 2002/061* (2013.01); *D10B 2509/06* (2013.01); *A61F 2250/0017* (2013.01); *A61F 2002/075* (2013.01); *A61F 2/07* (2013.01); *A61F 2/89* (2013.01); *A61F 2250/0018* (2013.01); *A61F 2250/0015* (2013.01)
 USPC .......................... 623/1.35; 623/1.13; 623/1.16

(58) Field of Classification Search
 None
 See application file for complete search history.

(56) References Cited

U.S. PATENT DOCUMENTS

| 5,425,765 | A | 6/1995 | Tiefenbrun et al. |
| 5,445,600 | A | 8/1995 | Abdulla |
| 6,514,286 | B1 | 2/2003 | Leatherbury et al. |
| 6,524,335 | B1 | 2/2003 | Hartley et al. |
| 6,942,879 | B2 | 9/2005 | Humes |
| 7,678,141 | B2 * | 3/2010 | Greenan et al. ............. 623/1.13 |
| 2002/0058992 | A1 * | 5/2002 | Greenhalgh ................ 623/1.35 |
| 2003/0199967 | A1 | 10/2003 | Hartley et al. |
| 2004/0106972 | A1 | 6/2004 | Deaton |

(Continued)

FOREIGN PATENT DOCUMENTS

| EP | 1 847234 B1 | 10/2007 |
| WO | WO 2005/034810 A1 | 4/2005 |
| WO | 2009/056644 | 5/2009 |

OTHER PUBLICATIONS

Branched and Fenestrated Stent-Grafts presentation, Tim Chuter, MD, 15 pages.

(Continued)

*Primary Examiner* — Thomas J Sweet
*Assistant Examiner* — Rebecca Preston
(74) *Attorney, Agent, or Firm* — Brinks Gilson & Lione

(57) ABSTRACT

An endoluminal prosthesis with a moveable fenestration including a tubular graft body having a proximal end, a distal end, a surface plane at least one fenestration having a perimeter disposed in a sidewall of the tubular body between the proximal end and the distal end, a first biocompatible graft material, and a second biocompatible graft material adjacent to and surrounding the perimeter of the at least one fenestration. The second biocompatible graft material has at least one characteristic different from the first biocompatible graft material and is more flexible than the first biocompatible graft material and is movable relative to the surface plane of the tubular graft body.

10 Claims, 4 Drawing Sheets

(56) References Cited

U.S. PATENT DOCUMENTS

| | | |
|---|---|---|
| 2004/0215327 A1 | 10/2004 | Doig et al. |
| 2005/0102021 A1 | 5/2005 | Osborne |
| 2005/0131517 A1* | 6/2005 | Hartley et al. ............... 623/1.13 |
| 2005/0131518 A1 | 6/2005 | Hartley et al. |
| 2005/0149166 A1 | 7/2005 | Schaeffer et al. |
| 2005/0171597 A1 | 8/2005 | Boatman et al. |
| 2005/0171598 A1 | 8/2005 | Schaeffer |
| 2005/0182476 A1 | 8/2005 | Hartley et al. |
| 2005/0222668 A1 | 10/2005 | Schaeffer et al. |
| 2005/0222669 A1 | 10/2005 | Purdy |
| 2005/0228488 A1* | 10/2005 | Nazzaro ...................... 623/1.26 |
| 2005/0273155 A1 | 12/2005 | Bahler et al. |
| 2006/0058864 A1 | 3/2006 | Schaeffer et al. |
| 2006/0247760 A1* | 11/2006 | Ganesan et al. ............. 623/1.16 |
| 2007/0276468 A1* | 11/2007 | Holzer et al. ................ 623/1.35 |
| 2009/0030502 A1 | 1/2009 | Sun et al. |
| 2009/0240316 A1* | 9/2009 | Bruszewski ................. 623/1.13 |
| 2009/0259290 A1* | 10/2009 | Bruszewski et al. ......... 623/1.13 |
| 2009/0264821 A1* | 10/2009 | Mafi et al. ................ 604/103.01 |

OTHER PUBLICATIONS

Branched Stent-Grafts presentation, Tim Chuter, MD, 15 pages.
Branched Stent-Grafts presentation, Tim Chuter, MD, 2002, 30 pages.
Branched Stent-Grafts presentation, Tim Chuter, MD, 29 pages.
Endovascular AAA Repair presentation, Tim Chuter, MD, 2002, 56 pages.
Endovascular AAA Repair presentation, Tim Chuter, MD, 2002, 44 pages.
Endovascular AAA Repair presentation, Tim Chuter, MD, Division of Vascular Surgery, University of California San Francisco, updated Sep. 2002, Part 1—50 pgs and Part 2—44pgs.

* cited by examiner

PROSTHESIS WITH MOVEABLE FENESTRATION

This application claims the benefit of priority from U.S. Provisional Application No. 61/093,202, filed Aug. 29, 2008, which is incorporated by reference.

TECHNICAL FIELD

This invention relates to endoluminal medical devices for implantation within the human or animal body for treatment of endovascular disease.

BACKGROUND OF THE INVENTION

The functional vessels of human and animal bodies, such as blood vessels and ducts, occasionally weaken or even rupture. For example, the aortic wall can weaken, resulting in an aneurysm.

One surgical intervention for weakened, aneurismal, or ruptured vessels involves the use of an endoluminal prosthesis to provide some or all of the functionality of the original, healthy vessel and/or preserve any remaining vascular integrity by replacing a length of the existing vessel wall that spans the site of vessel failure. Stent grafts for endoluminal deployment are generally formed from a tube of a biocompatible material in combination with one or more stents to maintain a lumen. Stent grafts effectively exclude the defect by sealing both proximally and distally the defect, and shunting blood through its length.

In many cases, however, the damaged or defected portion of the vasculature may include a branch vessel. For example, in the case of the abdominal aorta, there are at least three major branch vessels, including the celiac, mesenteric, and renal arteries, leading to various other body organs. Thus, when the damaged portion of the vessel includes one or more of these branch vessels, some accommodation must be made to ensure that the prosthesis does not block or hinder blood flow through the branch vessel.

Attempts to maintain blood flow to branch vessels have included providing one or more fenestrations or holes in the sidewall of the prosthesis. Conventionally, a balloon expandable bare stent is deployed into the renal arteries through the fenestration in the main graft to assure alignment is maintained while the stent-graft is being delivered (e.g., manipulated) and continues to maintain patency post-procedure. The arterial tree is constantly under pulsatile motion due to the flow of blood through the arteries. Thus, the deployed bare metal secondary stent is often under severe and complicated loading conditions which must be borne entirely through the narrow interface presented by fenestrated prosthesis and the bare secondary stent. These conditions may cause deterioration of the secondary stent, and may put the patient at risk of injury. Furthermore, since conventional fenestrated grafts have a fixed interface, there is little room for error when deploying the prosthesis for treatment of the aneurysm. The deployment of the prosthesis has to be extremely precise to assure that the fenestrations are aligned with the branch vessels. If these branch vessels are blocked by the prosthesis, the original blood circulation is impeded, and the patient can suffer. The blockage of any branch vessel is usually associated with unpleasant or even life-threatening symptoms.

SUMMARY

One aspect of an endoluminal prosthesis including a tubular graft body having a proximal end, a distal end, a surface plane, at least one fenestration having a perimeter disposed in a sidewall of the tubular body between the proximal end and the distal end, a first biocompatible graft material, and a second biocompatible graft material adjacent to and surrounding the perimeter of the at least one fenestration. The second biocompatible graft material has at least one characteristic different from the first biocompatible graft material and is more flexible than the first biocompatible graft material and is movable relative to the surface plane of the tubular graft body.

In another aspect, an implantable prosthesis for treatment of a main vessel defect near one or more branch vessels includes a graft comprising a first biocompatible graft material forming a tubular main body defining a lumen with a proximal end, a distal end, and a surface plane, at least one fenestration having a perimeter positioned intermediate the proximal and distal ends disposed within a sidewall of the main body, the sidewall comprising a second biocompatible graft material adjacent to and surrounding the fenestration, the second biocompatible graft material having at least one characteristic different from the first biocompatible material and is defined by a woven fabric comprising yarns aligned in a first direction interwoven with yarns aligned in a second direction, where yarns aligned in the first direction are increased and decreased while the yarns in the second direction are held constant to form a protrusion. The second biocompatible graft material is of a greater flexibility than the first biocompatible material such that movement of the fenestration relative to the surface plane of the main graft is facilitated and where the second biocompatible graft material lies in a different plane than the surface plane.

In yet another aspect, a method of producing an endoluminal prosthesis graft, including the steps of: providing textile yarns of a first biocompatible graft material to be aligned in a first direction and a second direction, weaving the textile yarns to produce a woven graft having a surface plane, introducing textile yarns of a second biocompatible graft material in the first direction while keeping the number of textile yarns in the second direction constant, withdrawing the added textile yarns in the first direction at the same rate to create a protrusion, and creating a fenestration through the protrusion, where the second biocompatible material is adjacent to and surrounding the fenestration and is moveable relative to the surface plane of the woven graft.

The second biocompatible material may be the same material used for the graft or a different material so long as the graft material surrounding the fenestration has sufficient give or flexibility to permit a branch vessel device inserted through the fenestration to move relative to the fenestration in response to biological or other forces. For example, the second biocompatible material may comprise a graft material of a heavier denier than the graft material of the main body to provide more durability to the flexible fenestration. In one example, the graft material surrounding the fenestration may be a flexible, tapered sleeve integrally formed into the graft material.

DETAILED DESCRIPTION

Figure 1:
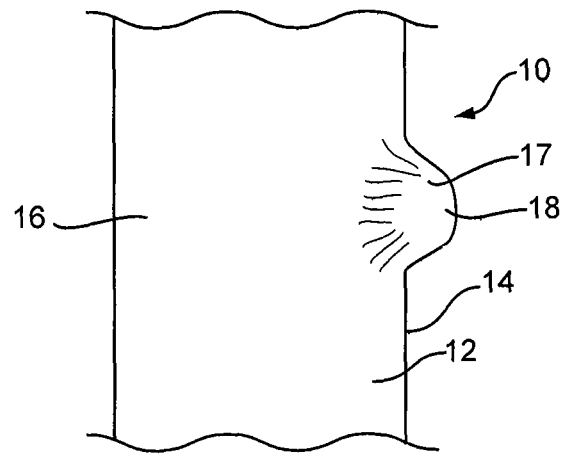
FIG. 1 depicts a prosthesis with a protrusion of graft material.

Unless defined otherwise, all technical and scientific terms used herein have the same meaning as commonly understood to one of ordinary skill in the art to which this invention belongs.

The terms "distal" and "distally" are intended to refer to a location or direction that is, or a portion of a device that when implanted is further downstream in the direction of or with respect to blood flow. The terms "proximal" and "proximally" are intended to refer to a location or direction that is, or a portion of a device that when implanted is further upstream in the direction of or with respect to blood flow.

The term "prosthesis" means any replacement for a body part or function of that body part. It can also mean a device that enhances or adds functionality to a physiological system.

The term "tubular" refers to the general shape of an endoluminal device which allows the module to carry fluid along a distance or fit within a tubular structure such as an artery. Tubular prosthetic devices include single and both branched and bifurcated devices.

The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "stent" means any device or structure that adds rigidity, expansion force or support to a prosthesis. A stent is used to obtain and maintain the patency of the body passageway while maintaining the integrity of the passageway. Also, the stent may be used to form a seal. The stent may be located on the exterior of the device, the interior of the device, or both. A stent may be self-expanding, balloon-expandable or may have characteristics of both. A variety of other stent configurations are also contemplated by the use of the term "stent."

The term "yarn" refers to a length of a continuous thread or strand of one or more filaments or fibers, with or without twist, suitable for weaving, knitting or otherwise intertwining to form a textile fabric.

The term "graft" or "graft material" describes an object, device, or structure that is joined to or that is capable of being joined to a body part to enhance, repair, or replace a portion or a function of that body part. A graft by itself or with the addition of other elements, such as structural components, can be an endoluminal prosthesis. The graft comprises a single material, a blend of materials, a weave, a laminate, or a composite of two or more materials. The graft can also comprise polymer material that may be layered onto the mandrel of the present invention. Preferably, polymers of the present invention, although added in layers onto the mandrel, after curing, result in one layer that encapsulates a stent or woven graft. This also aids in decreasing the incidence of delamination of the resulting endovascular prosthesis. A stent may be attached to a graft to form a "stent graft."

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

"Longitudinally" refers to a direction, position or length substantially parallel with a longitudinal axis of a reference, and is the length-wise component of the helical orientation.

"Circumferentially" refers to a direction, position, or length that encircles a longitudinal axis of reference. Circumferential is not restricted to a full 360° circumferential turn nor a constant radius.

The terms "patient," "subject," and "recipient" as used in this application refer to any mammal, especially humans.

Prostheses with moveable fenestrations are provided comprising a wall made from graft material formed into a tube. A lumen extends longitudinally throughout the prosthesis. The moveable fenestration is configured such that it permits a branch prosthesis that is inserted into and through the fenestration to move relative to the plane of the wall of the main prosthesis. The moveable fenestration may be a flexible fenestrated sleeve.

In some aspects, the flexible fenestrated sleeve is tapered. Further, the flexible fenestrated sleeve may have ability to move telescopically. Once a secondary branch stent is deployed into a branch vessel through the flexible fenestrated sleeve, the flexible fenestrated sleeve works to maintain alignment of the fenestration and a branch vessel.

FIG. 1 illustrates one aspect of a prosthesis 10 in accordance with the present invention. The prosthesis 10 comprises a tubular graft body 12 having a surface plane configured to be placed within a diseased vessel of a patient. The prosthesis 10 is comprised of a first biocompatible graft material 16 and includes a proximal end and a distal end. The graft material 16 may be constructed from a biocompatible textile fabric, a polymer, biomaterial, or a composite thereof. Examples of biocompatible materials from which textile graft material can be formed include polyesters, such as polyethylene terephthalate; fluorinated polymers, such as polytetrafluoroethylene (PTFE) and fibers of expanded PTFE; and polyurethanes. Preferably, the graft material 16 is a woven polyester. More preferably, the graft material 16 is a polyethylene terephthalate (PET), such as DACRON® (DUPONT, Wilmington, Del.) or TWILLWEAVE MICREL® (VASCUTEK, Renfrewshire, Scotland).

In this aspect, the tubular graft body 12 includes a sidewall 14 containing a protrusion 18 of a second biocompatible graft material 17. The protrusion 18 is integrally formed from the body of the tubular graft body 12, and extends outward radially in a bubble like formation. The protrusion 18 is comprised of a second biocompatible graft material and may be created during the weaving process used to create the tubular graft body 12. The second biocompatible graft material may have at least one characteristic different than the first biocompatible graft material. In addition, the second biocompatible graft material may be more flexible than the first biocompatible graft material. The prosthesis 10 may comprise any kind of weave. For example, the tubular graft body 12 may include, but is not limited to, weaves such as plain weaves, basket weaves, rep or rib weaves, twill weaves (e.g., straight twill, reverse twill, herringbone twill), satin weaves, and double weaves (e.g., double-width, tubular double weave, reversed double weave). Desirably, the weave comprises a tubular double layer weave. The tubular graft body 12 and the protrusion 18 may be woven in any suitable manner. For example, the fabric may be woven on a table loom, a floor loom, a jacquard loom, a counterbalance loom, a jack loom, or an upright loom. Desirably, the fabric is woven on a floor loom. The fabric may have any configuration possible, but preferably has warp and weft yarns. In one aspect, both the warp yarns and the weft yarns are textile yarns.

During the weaving process to create the graft, the sett and pick count are kept constant. The sett may be between about 50 and about 300 ends per inch and the pick count may be between about 50 and about 300 picks per inch. An "end" refers to an individual warp yarn, and a "pick" refers to an individual weft yarn. In one aspect, the textile graft comprises a plain weave having 150 ends per inch and 250 picks per inch.

In order to create the protrusion 18, the number of warp yarns used while weaving the prosthesis 10 is increased in the region where the protrusion 18 is desired. While the additional warp yarns are weaved into the prosthesis 10, the number of weft yarns is kept constant. By increasing the number of warp yarns while holding the number of weft yarns constant, the second biocompatible graft material 17 expands outwardly in the radial direction. The number of warp yarns is increased until a pre-determined diameter has been reached. The predetermined diameter of the protrusion 18 may range from about 2 mm to about 10 mm. Once the desired diameter for the protrusion 18 is reached, the number of warp yarns introduced into the weaving apparatus is decreased until the number of warp yarns is equal to the number of weft yarns used to form the remainder of the graft 12. During this weaving process, the sett and pick count are kept constant due to the increasing diameter of the graft 12 in the area of the protrusion 18. Further, the density of the protrusion 18 is kept constant by weaving the weft yarns at the same speed.

In another aspect, the density of the protrusion 18 may be altered based on the needs of the patient. For example, one may achieve a protrusion 18 of an increased density in the direction of the warp yarns by weaving the weft yarns at a slower speed and by changing the sett and pick count of the weave. This increased density provides increased structural support for the graft 12, which can benefit a patient suffering from vessels having an advanced diseased state. Alternatively, the density of the protrusion 18 in the direction of the warp yarns may be decreased by weaving the weft yarns at a faster speed. Further, the change in density allows for increased control of the desired shape of the protrusion 18.

In other aspects, yarns having a heavier denier may be used to create the protrusion 18 in order to increase the durability of the protrusion 18. For example, the graft material 16 of the tubular graft body 12 may be comprised of a plurality of yarns having a denier of about 100. In order to provide added strength and durability for the flexible sleeve, the second biocompatible graft material 17 comprised of a plurality of yarns having a denier of about 120 may be weaved into the tubular graft body to form the protrusion 18 during the process used to produce the prosthesis. The protrusion 18 may also be tapered in order to generate a cone effect at the position of the fenestration.

Figure 2:
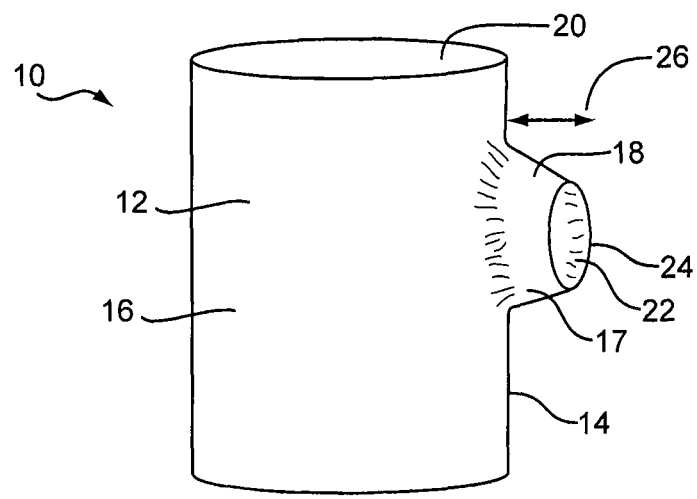
FIG. 2 depicts a prosthesis having a flexible fenestration.

FIG. 2 illustrates one aspect of a tubular graft body 12 containing a fenestration 22. The fenestration 22 has a perimeter and is disposed through the protrusion 18 and the sidewall 14 such that the fenestration 22 is in fluid communication with a lumen 20 of the graft body 12. In some aspects, the fenestration 22 is created through the protrusion 18 by applying heat to the center of the protrusion 18 at a temperature of at least 260° C. The application of heat causes the fibers of the graft material 16 to melt together, which helps prevent fraying. Alternatively, the fenestration 22 may be created by cutting the protrusion 18 in its center in order to form an opening for the fenestration 22. In this aspect, an adhesive may be applied to edges of the perimeter of the fenestration 22 to prevent the fibers from fraying. Thus, the second biocompatible graft material 17 is adjacent to and surrounding the perimeter of the fenestration 22, and the second biocompatible graft material may be in a different plane than the surface plane of the tubular graft body 12. The second biocompatible graft material 17 surrounding the fenestration 22 is moveable relative to the surface plane of the tubular graft body 12. The diameter of the fenestration 22 may be modified depending on the size of the patient's vessels. The diameter of the fenestration 22 may range from about 2 mm to about 10 mm. Preferably, the second biocompatible graft material surrounding the fenestration 22 has a diameter that is at least 10% greater than the diameter of the graft.

As shown in FIG. 2, a nitinol ring 24 may be placed about the perimeter of the fenestration 22 in order to prevent it from closing. The nitinol ring 24 may be secured about the perimeter of the fenestration 22 by suture material. In other aspects, the fenestration 22 may be prevented from closing by placing a seam comprised of biocompatible materials, such as suture material, about the perimeter of the fenestration 22. Any excess material suture material present after creating the seam may be removed by cutting the material within the circumference of the fenestration 22.

The second biocompatible graft material 17 surrounding the fenestration 22 may be in a radially telescopic relationship with respect to the surface plane of the tubular graft body 12. As such, the second biocompatible graft material 17 surrounding the fenestration 22 may be configured to move telescopically within a certain range. The telescopic range 26 spans from the edge of the fenestration 22 to the sidewall 14 of the tubular graft body 12. The telescopic range 28 allows the moveable fenestration 22 to be pushed flush with the diameter of the tubular graft body 12. Once the fenestration 22 is flush with the wall 14 of the tubular graft body 12, a wrinkle is formed by the second biocompatible graft material 17 adjacent to and surrounding the fenestration 22. This wrinkle provides for the relative movement of the fenestration 22 and the tubular graft body 12 without transmitting significant load to the fenestration 22. This movement reduces the amount of stress applied to a secondary branch stent when it is deployed into a branch vessel.

In some aspects, the second biocompatible material forming the protrusion 18 or area surrounding the fenestration 22 may be comprised of biocompatible materials that are different than the first biocompatible material used to form the tubular graft body 12. Examples of suitable biocompatible materials include: polyurethane, silicone infused polyurethane, such as Thoralon® (Thoratec, Pleasanton, Calif.), or Biospan®, Bionate®, Elasthane®, Pursil® And Carbosil® (Polymer Technology Group, Berkeley, Calif.).

Figure 3:
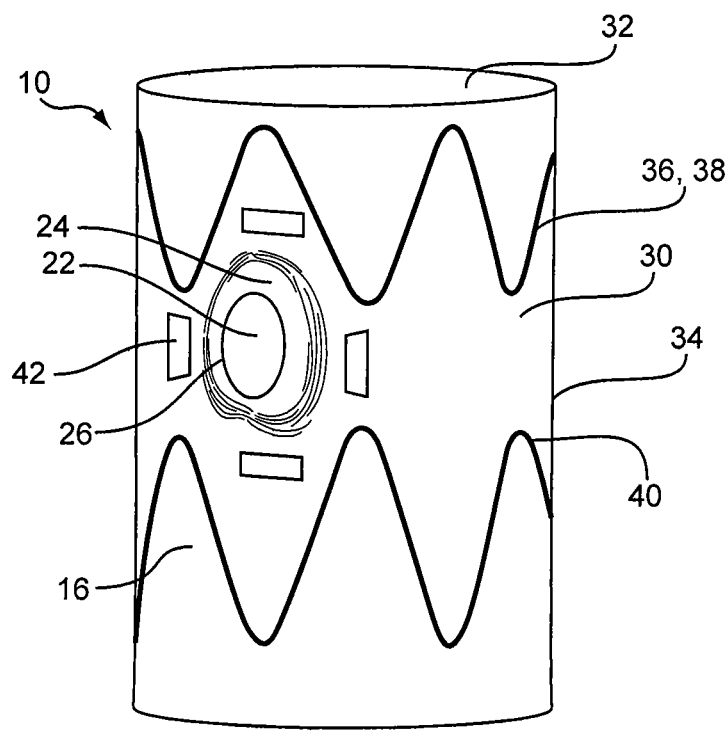
FIG. 3 shows a perspective view of a prosthesis with an integral flexible fenestration.
Figure 4:
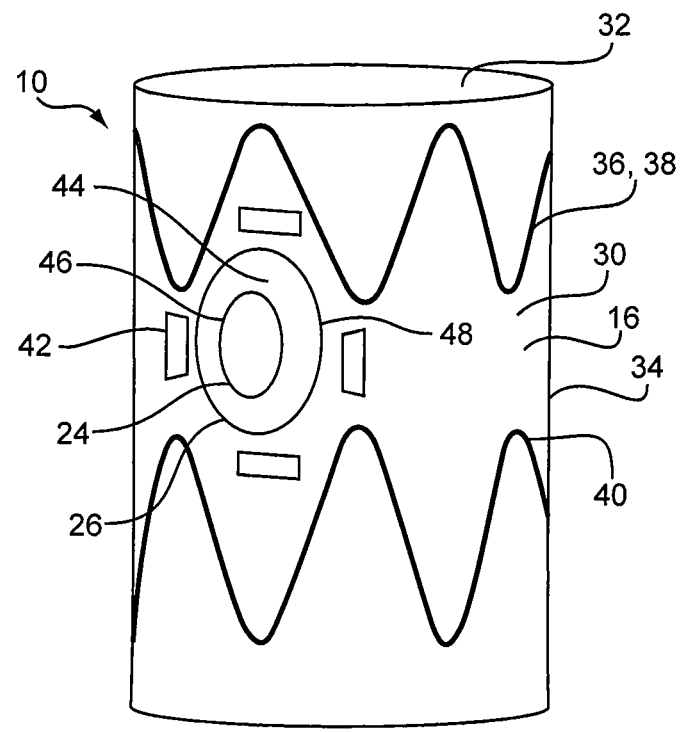
FIG. 4 shows a perspective view of a prosthesis having a flexible fenestration.

FIGS. 3 and 4 illustrate aspects of a prosthesis for deployment in the abdominal aorta. As seen in FIG. 3, the prosthesis 10 comprises a tubular stent graft 30 with a wall 34 and a lumen 32 disposed longitudinally therein. The tubular stent graft 30 includes a fenestration 22 disposed through the second biocompatible graft material added during the weaving process. The fenestration 22 is in communication with the lumen 32 of the tubular stent graft 30. The prosthesis 10 further comprises a plurality of expandable stents 36 affixed to the wall 34 of the tubular stent graft 30. The expandable stents 36 maintain the patency of the prosthesis and ensure adequate sealing against the surrounding vascular tissue. The Z-stent design is preferred for straight sections of the aorta; it provides both significant radial force as well as some longitudinal support. In some instances, it may be desirable to affix some of the stents to the internal surface of the prosthesis. Stent amplitude, spacing and stagger are preferably optimized for each prosthesis design. The expandable stents 36 include struts 38 that are spaced apart from each other. The strut spacing is measured from peak-to-peak. The peaks 40 of the struts 38 may be staggered for minimal contact with each other.

The stent may be formed from nitinol, stainless steel, tantalum, titanium, gold, platinum, inconel, iridium, silver, tungsten, cobalt, chromium, or another biocompatible metal, or alloys of any of these. Examples of other materials that may be used to form stents include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these. Preferably, the stent is a nitinol or stainless steel stent. Any of the stents mentioned herein may have barbs to help decrease prosthesis migration.

As illustrated in FIG. 3, the fenestration 22 is flush with the diameter of the tubular stent graft 30. Radiopaque markers 42 may be placed around the fenestration 22 in order to assist with proper alignment of the tubular stent graft 30 when deployed within the patient. The radiopaque markers 42 may be sewn to the wall 34 of the tubular stent graft 30. Radiopaque materials such as gold, platinum, tungsten, or any other high density material may be used.

In another aspect, depicted in FIG. 4, an opening is cut into the wall 34 of the tubular stent graft 30, and a flexible tube 44 is affixed about the opening. The tube 44 also includes a first end 46 and a second end 48, and it may also be tapered. The tube 44 is affixed to the sidewall 34 of the tubular graft body 30 by suturing the proximal end of the tube 44 circumferentially about the opening. The second end 48 of the tube 44 is in communication with the opening. In order to keep the fenestration in an open configuration, a nitinol ring 26 may be placed about the second end 48 of the solid tube 44. The second end 48 of the solid tube 44 may also be maintained in an open configuration by means other suitable means known by a person of the ordinary skill in the art.

Figure 5:
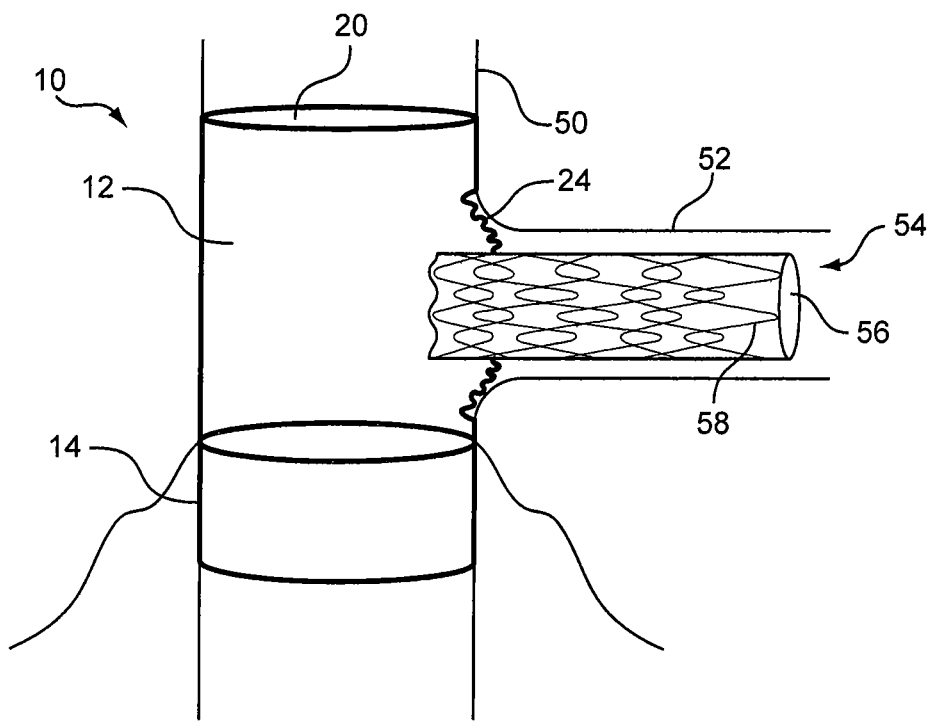
FIG. 5 shows a cross-sectional view of a prosthesis where a secondary branch stent is deployed into a branch vessel.

FIG. 5 depicts an exemplary prosthesis deployed in a patient. The prosthesis 10 comprising a tubular graft body 12 is deployed in the main vessel 50 of the patient. The tubular graft body 12 includes a moveable fenestration 22 in communication with the lumen 20. A secondary branch prosthesis 54, such as a stent, is deployed into a branch vessel 52 to maintain the alignment of the flexible fenestration 22 and the branch vessel 52. The secondary branch prosthesis 54 is formed from biocompatible material and is comprised of a plurality of stents having struts 58 that extend circumferentially about a longitudinal axis and form a lumen 56 extending longitudinally within the secondary branch prosthesis 54. Examples of acceptable biocompatible metals are discussed above. The fenestration 22 receives the secondary branch prosthesis 54. The second biocompatible graft material surrounding the fenestration 22 wrinkles when it is flush with the diameter of tubular graft body 12, which allows for some movement of the fenestration 22 relative to the surface plane of the tubular graft body 12 without transmitting direct force to the secondary branch prosthesis 54.

Figure 6A:
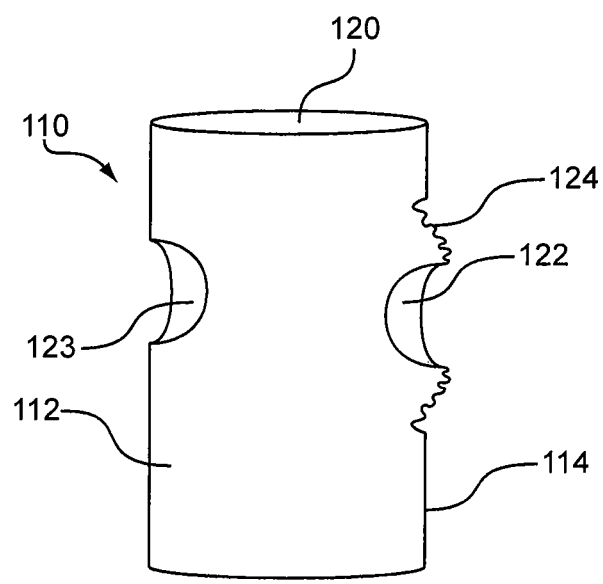
FIG. 6A shows a prosthesis with a flexible fenestration sleeve and a second fenestration in the wall of the prosthesis.
Figure 6B:
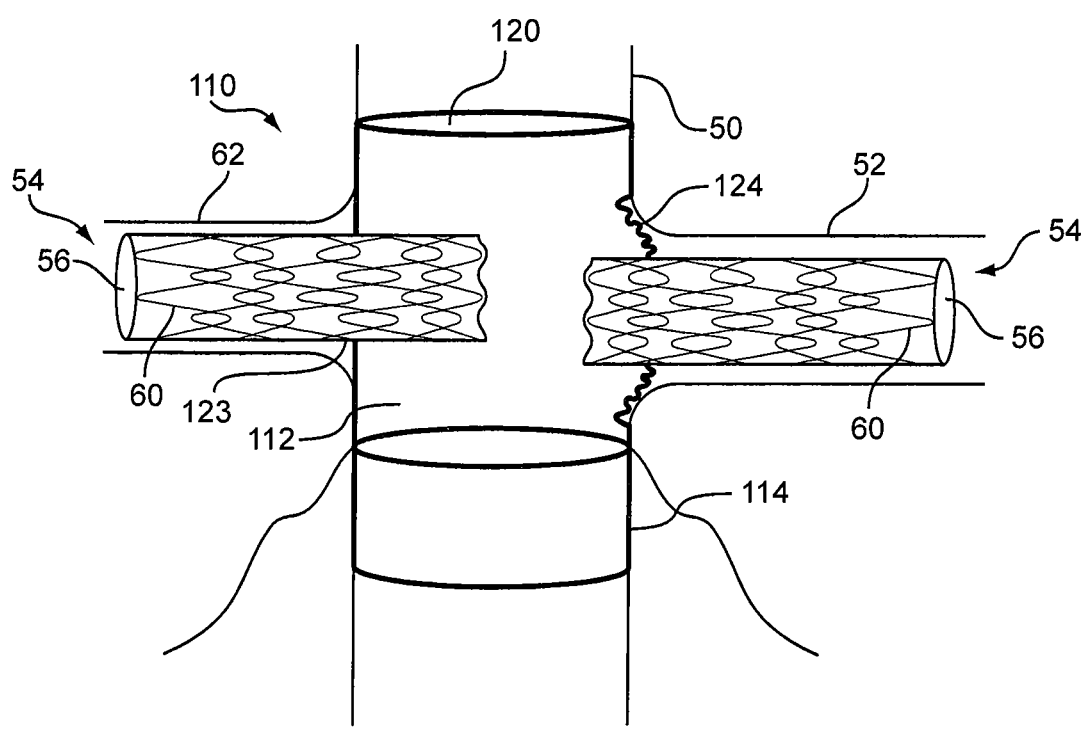
FIG. 6B shows the prosthesis of FIG. 6A where secondary branch stents are deployed into branch vessels.

FIGS. 6A and 6B illustrate a further aspect of the present invention. As shown by FIG. 6A, a prosthesis 110 includes a tubular graft body 112 formed of a first biocompatible graft material comprising a first fenestration 122 and a second fenestration 123 disposed through the sidewall 114 of the tubular graft body 112, where a second biocompatible material 124 is surrounding and adjacent to the first fenestration 122. The tubular graft body 112 also includes a lumen 120. This aspect is suitable for implantation in an abdominal aortic aneurysm where two branch vessels may be occluded during the deployment of the tubular graft. The second fenestration 123 may be a fixed fenestration or it may be disposed through a protrusion formed from the weaving of a second biocompatible graft material. The second fenestration 123 is in communication with the lumen 120 of the tubular graft body 112. Radiopaque markers (not shown) may be placed about the flexible fenestrated sleeve and the second fenestration 123 in order to assist the physician with placement of the tubular graft body 112.

The second fenestration 123 may be created in the tubular graft body 112 relative to the location of the first fenestration 122 on the tubular graft body 112. For example, patients suffering from abdominal aortic aneurysms may have branch vessels that are not aligned. Thus, in order to facilitate alignment of the tubular graft body 112 within the vasculature of the patient, the second fenestration 123 may be formed after the first fenestration 122 is created from a protrusion comprised of second biocompatible graft material 124. In addition, the length of the tubular graft body 112 may also be altered relative to the flexible fenestration 122 in order to configure the tubular graft body 112 with vasculature of the patient.

As shown in FIG. 6B, a tubular graft body 112 of the example shown in FIG. 6A is deployed in the main vessel 50 of the patient to occlude an aneurysm. The fenestration 122 is flush with the diameter of the sidewall 114 of the tubular graft body 112 creating a wrinkle comprised of the second biocompatible graft material 124 surrounding the fenestration 122. Two secondary branch prostheses 54, having a plurality of struts 60 and having a central lumen 56, are deployed in the branch vessels. The secondary branch prostheses 54 help maintain alignment of the tubular graft body 112 to provide for proper blood flow to the branch vessels 52, 62. The secondary branch prostheses 54 are received through the first fenestration 122 and the second fenestration 123, respectively.

In some instances, the first fenestration 122 may not be aligned with the branch vessel 52. In this example, the wrinkle of graft material of the first fenestration 122 allows for some movement of the first fenestration 122 relative to the surface plane of the tubular graft body 112 without transmitting direct force to the secondary branch stent 54, which helps to provide alignment between the first fenestration 122 and the branch vessel 52.

Throughout this specification various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents, that are intended to define the spirit and scope of this invention.

The invention claimed is:

1. An endoluminal prosthesis, comprising:
   a tubular graft body comprising:
   a proximal end;
   a distal end;
   a surface plane;
   at least one fenestration having a perimeter disposed in a sidewall of the tubular graft body between the proximal end and the distal end;
   a first biocompatible graft material; and
   a second biocompatible graft material adjacent to and surrounding the perimeter of the at least one fenestration and defining a region of second biocompatible graft material adjacent to and surrounding the perimeter of the at least one fenestration,
   where the second biocompatible graft material has at least one characteristic different from the first biocompatible graft material,
   where the second biocompatible material is more flexible than the first biocompatible graft material such that the at least one fenestration is movable relative to the surface plane of the tubular graft body,
   where the region of the second biocompatible graft material is defined by a woven fabric comprising warp yarns aligned in a first direction interwoven with weft yarns aligned in a second direction,
   where the number of warp yarns aligned in the first direction are increased and then decreased while the weft yarns aligned in the second direction are held constant such that a protrusion is formed in an area of the tubular graft body comprising the at least one fenestration, and
   where the region of the second biocompatible graft material comprises between about 50 and about 300 weft yarns per inch and between about 50 and about 300 warp yarns per inch.

2. The endoluminal prosthesis of claim 1, where the region of the second biocompatible graft material lies in a different plane than the surface plane.

3. The endoluminal prosthesis of claim 1, where the region of the second biocompatible graft material provides a radially telescoping relationship of the region of the second biocompatible graft material relative to the surface plane of the tubular graft body.

4. The endoluminal prosthesis of claim 1, where the region of the second biocompatible graft material is composed of yarn having a higher denier than yarn of the first biocompatible graft material.

5. The endoluminal prosthesis of claim 1, where the yarns aligned in the first direction comprise biocompatible polyurethane.

6. The endoluminal prosthesis of claim 1, where a density of the second biocompatible graft material is equal to a density of the first biocompatible graft material.

7. The endoluminal prosthesis of claim 1, where a density of the second biocompatible graft material is greater than a density of the first biocompatible graft material.

8. The endoluminal prosthesis of claim 1, where at least a portion of the region defined by the second biocompatible graft material comprises a tube having a first end and a second end.

9. The endoluminal prosthesis of claim 6, where the region of the second biocompatible graft material extends a distance of at least 10% of a diameter of the tubular graft body.

10. The endoluminal prosthesis of claim 1, where the region of the second biocompatible graft material has a diameter of about 2 to about 10 millimeters.

\* \* \* \* \*